United States Patent
Murdock

[11] Patent Number: 6,071,508
[45] Date of Patent: *Jun. 6, 2000

[54] PREPARATION OF FORMULATIONS FOR ELECTROTRANSPORT DRUG DELIVERY

[75] Inventor: Thomas Owen Murdock, Vadnais Heights, Minn.

[73] Assignee: Alza Corporation, Mountain View, Calif.

[ * ] Notice: This patent is subject to a terminal disclaimer.

[21] Appl. No.: 08/993,213

[22] Filed: Dec. 18, 1997

Related U.S. Application Data

[63] Continuation of application No. 08/433,173, May 3, 1995, Pat. No. 5,853,383.

[51] Int. Cl.⁷ ........................ A61K 31/785; A61K 31/74; A61F 13/00
[52] U.S. Cl. ................... 424/78.12; 424/78.1; 424/449; 424/78.08; 424/78.11
[58] Field of Search .................. 424/449, 78.1, 424/78.12, 78.11, 78.08; 604/20

[56] References Cited

U.S. PATENT DOCUMENTS

| | | | |
|---|---|---|---|
| 4,203,440 | 5/1980 | Theeuwes | 604/892.1 |
| 4,203,441 | 5/1980 | Theeuwes | 604/892.1 |
| 4,711,777 | 12/1987 | Tan et al. | 514/158 |
| 4,722,726 | 2/1988 | Sanderson et al. | 604/20 |
| 4,780,322 | 10/1988 | Martani et al. | 424/78.11 |
| 4,847,077 | 7/1989 | Raghunathan | 424/495 |
| 4,894,239 | 1/1990 | Nonomura et al. | 424/497 |
| 4,915,685 | 4/1990 | Petelenz et al. | 604/20 |
| 5,080,646 | 1/1992 | Theeuwes et al. | 604/20 |
| 5,147,296 | 9/1992 | Theeuwes et al. | 604/20 |
| 5,169,382 | 12/1992 | Theeuwes et al. | 604/20 |
| 5,169,383 | 12/1992 | Gyory et al. | 604/20 |
| 5,250,023 | 10/1993 | Lee et al. | 604/20 |

FOREIGN PATENT DOCUMENTS

| | | |
|---|---|---|
| 0299615 | 6/1987 | European Pat. Off. . |
| 0318776 | 6/1989 | European Pat. Off. . |
| 2265088 | 9/1993 | United Kingdom . |
| 9317017 | 9/1993 | WIPO . |
| 9317755 | 9/1993 | WIPO . |
| 9505815 | 3/1995 | WIPO . |

*Primary Examiner*—Thurman K. Page
*Assistant Examiner*—Todd D Ware
*Attorney, Agent, or Firm*—Owen J. Bates; D. Byron Miller; Steven F. Stone

[57] ABSTRACT

A method is provided for preparing drug formulations suitable for electrotransport drug delivery. The drug to be delivered, present in salt form, is contacted with an ion exchange material prior to incorporation into the reservoir (26) of an electrotransport delivery system (10). In this way, the drug salt is partially or completely neutralized. This technique is useful for adjusting the pH of the drug formulation without incorporating extraneous materials, e.g., competing ions or the like, into the reservoir (26).

19 Claims, 2 Drawing Sheets

PREPARATION OF FORMULATIONS FOR ELECTROTRANSPORT DRUG DELIVERY

This application is a continuation of Ser. No. 08/433,173 filed May 3, 1995, and now U.S. Pat. No. 5,853,383.

TECHNICAL FIELD

This invention relates generally to electrotransport drug delivery. More particularly, the invention relates to a method for adjusting the pH of drug formulations for incorporation into an electrotransport drug delivery system. The invention additionally relates to electrotransport drug delivery systems containing pH-adjusted drug formulations which are substantially free of contaminating materials, particularly ionic species which compete with the drug to be delivered.

BACKGROUND ART

The delivery of drugs through the skin provides many advantages; primarily, such a means of delivery is a comfortable, convenient and noninvasive way of administering drugs. The variable rates of absorption and metabolism encountered in oral treatment are avoided, and other inherent inconveniences—e.g., gastrointestinal irritation and the like—are eliminated as well. Transdermal drug delivery also makes possible a high degree of control over blood concentrations of any particular drug.

However, many drugs are not suitable for passive transdermal drug delivery because of their size, ionic charge characteristics and hydrophilicity. One method of overcoming this limitation in order to achieve transdermal administration of such drugs is the use of electrical current to actively transport drugs into the body through intact skin. The method of the invention relates to such an administration technique, i.e., to "electrotransport" or "iontophoretic" drug delivery.

Herein the terms "electrotransport", "iontophoresis", and "iontophoretic" are used to refer to the transdermal delivery of pharmaceutically active agents by means of an applied electromotive force to an agent-containing reservoir. The agent may be delivered by electromigration, electroporation, electroosmosis or any combination thereof. Electroosmosis has also been referred to as electrohydrokinesis, electroconvection, and electrically induced osmosis. In general, electroosmosis of a species into a tissue results from the migration of solvent in which the species is contained, as a result of the application of electromotive force to the therapeutic species reservoir, i.e., solvent flow induced by electromigration of other ionic species. During the electrotransport process, certain modifications or alterations of the skin may occur such as the formation of transiently existing pores in the skin, also referred to as "electroporation". Any electrically assisted transport of species enhanced by modifications or alterations to the body surface (e.g., formation of pores in the skin) are also included in the term "electrotransport" as used herein. Thus, as used herein, the terms "electrotransport", "iontophoresis" and "iontophoretic" refer to (1) the delivery of charged drugs or agents by electromigration, (2) the delivery of uncharged drugs or agents by the process of electroosmosis, (3) the delivery of charged or uncharged drugs by electroporation, (4) the delivery of charged drugs or agents by the combined processes of electromigration and electroosmosis, and/or (5) the delivery of a mixture of charged and uncharged drugs or agents by the combined processes of electromigration and electroosmosis.

Systems for delivering ionized drugs through the skin have been known for some time. British Patent Specification No. 410,009 (1934) describes an iontophoretic delivery device which overcame one of the disadvantages of the early devices, namely, the need to immobilize the patient near a source of electric current. The device was made by forming, from the electrodes and the material containing the drug to be delivered, a galvanic cell which itself produced the current necessary for iontophoretic delivery. This device allowed the patient to move around during drug delivery and thus required substantially less interference with the patient's daily activities than previous iontophoretic delivery systems.

In present electrotransport devices, at least two electrodes are used. Both of these electrodes are disposed so as to be in intimate electrical contact with some portion of the skin of the body. One electrode, called the active or donor electrode, is the electrode from which the drug is delivered into the body. The other electrode, called the counter or return electrode, serves to close the electrical circuit through the body. In conjunction with the patient's skin, the circuit is completed by connection of the electrodes to a source of electrical energy, e.g., a battery, and usually to circuitry capable of controlling current passing through the device. If the ionic substance to be driven into the body is positively charged, then the positive electrode (the anode) will be the active electrode and the negative electrode (the cathode) will serve as the counter electrode, completing the circuit. If the ionic substance to be delivered is negatively charged, then the cathodic electrode will be the active electrode and the anodic electrode will be the counter electrode.

Existing electrotransport devices additionally require a reservoir or source of the pharmaceutically active agent which is to be delivered or introduced into the body. Such drug reservoirs are connected to the anode or the cathode of the electrotransport device to provide a fixed or renewable source of one or more desired species or agents.

Thus, an electrotransport device or system, with its donor and counter electrodes, may be thought of as an electrochemical cell having two electrodes, each electrode having an associated half cell reaction, between which electrical current flows. Electrical current flowing through the conductive (e.g., metal) portions of the circuit is carried by electrons (electronic conduction), while current flowing through the liquid-containing portions of the device (i.e., the drug reservoir in the donor electrode, the electrolyte reservoir in the counter electrode, and the patient's body) is carried by ions (ionic conduction). Current is transferred from the metal portions to the liquid phase by means of oxidation and reduction charge transfer reactions which typically occur at the interface between the metal portion (e.g., a metal electrode) and the liquid phase (e.g., the drug solution). A detailed description of the electrochemical oxidation and reduction charge transfer reactions of the type involved in electrically assisted drug transport can be found in electrochemistry texts such as J. S. Newman, *Electrochemical Systems* (Prentice Hall, 1973) and A. J. Bard and L. R. Faulkner, *Electrochemical Methods, Fundamentals and Applications* (John Wiley & Sons, 1980).

As electrical current flows through an electrotransport device, oxidation of a chemical species takes place at the anode while reduction of a chemical species takes place at the cathode. Both of these reactions generate a mobile ionic species with a charge state (i.e., + or −) like that of the drug in its ionic form. Such a mobile ionic species is referred to as a "competitive species" or a "competitive ion" because the species competes with the drug for delivery by electrotransport.

Many drugs exist in both free acid/base form and a salt form. For example, a base drug may exist in either free base form or in salt form, e.g., in the form of an acid addition salt. One example of a base drug is lidocaine. In free base form, lidocaine is an amine. Lidocaine is also available as a hydrochloride acid addition salt. Conversely, an acid drug may exist in either free acid form or in the form of a salt made by reacting the free acid with a base. One example of an acid drug is salicylic acid. This drug also exists as a salt, typically as sodium salicylate. In general, the salt form of a drug is preferred over the free acid or free base form for electrotransport delivery since the salt form generally has much better water solubility and water is the preferred liquid solvent for electrotransport delivery due to its excellent biocompatibility.

Although the salt forms of drugs are likely to have higher water solubility, the pH of an aqueous solution of the drug salt may not be optimal from the standpoint of transdermal drug flux. For example, human skin exhibits a degree of permselectivity to charged ions which is dependant upon the pH of the donor solution of an electrotransport device. For anodic donor reservoir solutions, transdermal electrotransport flux of a cationic species (i.e., a cationic drug) is optimized when the pH of the donor solution is about 6 to 9, and more preferably about 7.5 to 8.5. For cathodic donor reservoir solutions, transdermal electrotransport flux of an anionic species (i.e., an anionic drug) is optimized when the pH of the donor solution is about 3 to 6, and more preferably about 3.5 to 5.

A problem which arises with the addition of pH-altering species (e.g., an acid or a base) to the drug solution in an electrotransport device is that extraneous ions having the same charge (i.e., same sign charge) as the drug are introduced into the solution. These ions generally compete with the therapeutic agent ions for electrotransport through the body surface. For example, the addition of sodium hydroxide to raise the pH of a cationic drug-containing solution will introduce sodium ions into the solution which will compete with the cationic drug for delivery by electrotransport into the patient, and thereby makes the electrotransport delivery less efficient since it takes more electric current to deliver a set amount of drug, i.e., less drug is delivered per unit of electrical current applied by the device due to competing ions carrying the current as opposed to the drug ions. The sodium ions, in this context, are termed "competing ions". As used herein, the term "competing ions" refers to ionic species having the same sign charge as the agent to be delivered by electrotransport, and which may take the place of the agent and be delivered through the body surface in its place. Similarly, conventional buffering agents used to buffer the pH of a donor reservoir solution can likewise result in the addition of competing ions into the donor reservoir which results in lower efficiency electrotransport drug delivery.

The present invention is addressed to a method for adjusting the pH of a drug formulation before it is incorporated into an electrotransport drug delivery system. The pH of any particular drug formulation may be adjusted either upward or downward, as desired. In this way, the flux of the drug through the skin may be optimized, as may the stability of particular drug/polymer matrix compositions. In this regard, it has been found that partially or completely neutralized drug formulations can yield a higher transdermal flux than the corresponding drug salt formulation, particularly when the drug is a divalent or polyvalent species.

In contrast to prior methods used to adjust the pH of a donor solution prior to electrotransport drug delivery, the present technique does not involve introduction of extraneous ions into the electrotransport system which would compete with the therapeutic agent ions for electrotransport through the body surface. For example, with cationic drugs, partial or complete neutralization by admixture with potassium hydroxide, sodium hydroxide, or the like would result in the incorporation of potassium ions, sodium ions, or the like, into the drug formulation, species which would in turn compete with the cationic drug for electrotransport delivery. Such a method reduces the efficiency of drug delivery and possibly results in other problems as well.

Additionally, the present method enables one to avoid the introduction of extraneous materials into the system, as may be associated with resins or the ite. U.S. Pat. No. 4,915,685 to Petelenz et al., for example, calls for incorporation of an ion exchange resin directly into the drug reservoir of an electrotransport delivery system. It is well known that industrial grade resins contain a number of impurities, which would of course be undesirable in a pharmaceutical formulation or device. The present invention avoids introduction of impurities in this manner.

Finally, it should be noted that the method of the invention, in providing a pH-adjusted drug formulation for electrotransport delivery, also facilitates buffering of the drug-containing composition. That is, the drug formulation will resist changes in pH which result from the addition of hydroxide ions or protons thereto.

DESCRIPTION OF THE INVENTION

Accordingly, it is a primary aspect of the invention to provide a method for preparing a drug formulation suitable for electrotransport delivery which overcomes the aforementioned limitations in the art, the method involving adjustment of the pH of a drug formulation prior to incorporation into an electrotransport delivery system.

It is another aspect of the invention to provide such a method which involves partial neutralization of a drug salt using an ion exchange material.

It is a further aspect of the invention to provide a method of optimizing the transdermal electrotransport flux of a drug by partially neutralizing the salt form of the drug prior to incorporation into an electrotransport drug delivery system.

It is still a further aspect of the invention to provide such a method which may be accomplished quickly and easily, without introduction of extraneous materials and/or competing ions into the drug formulation.

It is still a further aspect of the invention to provide an improved electrotransport drug delivery system containing a partially or completely neutralized drug formulation which is substantially free of contaminating materials, particularly competitive ionic species.

Additional aspects, advantages and novel features of the invention will be set forth in part in the description which follows, and in part will become apparent to those skilled in the art upon examination of the following, or may be learned by practice of the invention.

In one aspect of the invention, then, a method is provided for adjusting the pH of a drug formulation by contacting a drug salt contained therein with an ion exchange material. The ion exchange material is selected so that it is capable of exchanging hydroxyl ions for anionic counterions, in the case of cationic drugs, or exchanging hydrogen ions for cationic counterions, in the case of anionic drugs. The drug salt, typically contained in an aqueous solution, may be partially or completely neutralized, as desired; the degree of neutralization may be easily controlled by adjusting the relative quantities of drug salt and ion exchange material.

After the pH of the drug formulation is adjusted as desired, the ion exchange material is preferably removed from the drug solution using conventional techniques, and the drug formulation may then be incorporated into a suitable electrotransport drug delivery system.

In another aspect of the invention, an improved electrotransport drug delivery system is provided. The system contains a donor electrode, a counter electrode, a source of electrical power, and a reservoir containing the drug to be delivered, typically present as part of the donor electrode, with the improvement comprising the use of a drug formulation prepared using the presently disclosed process, such that the drug formulation in the drug reservoir of the electrotransport delivery system is substantially free of contaminating materials, particularly competitive ionic species.

MODES FOR CARRYING OUT THE INVENTION

Figure 1:
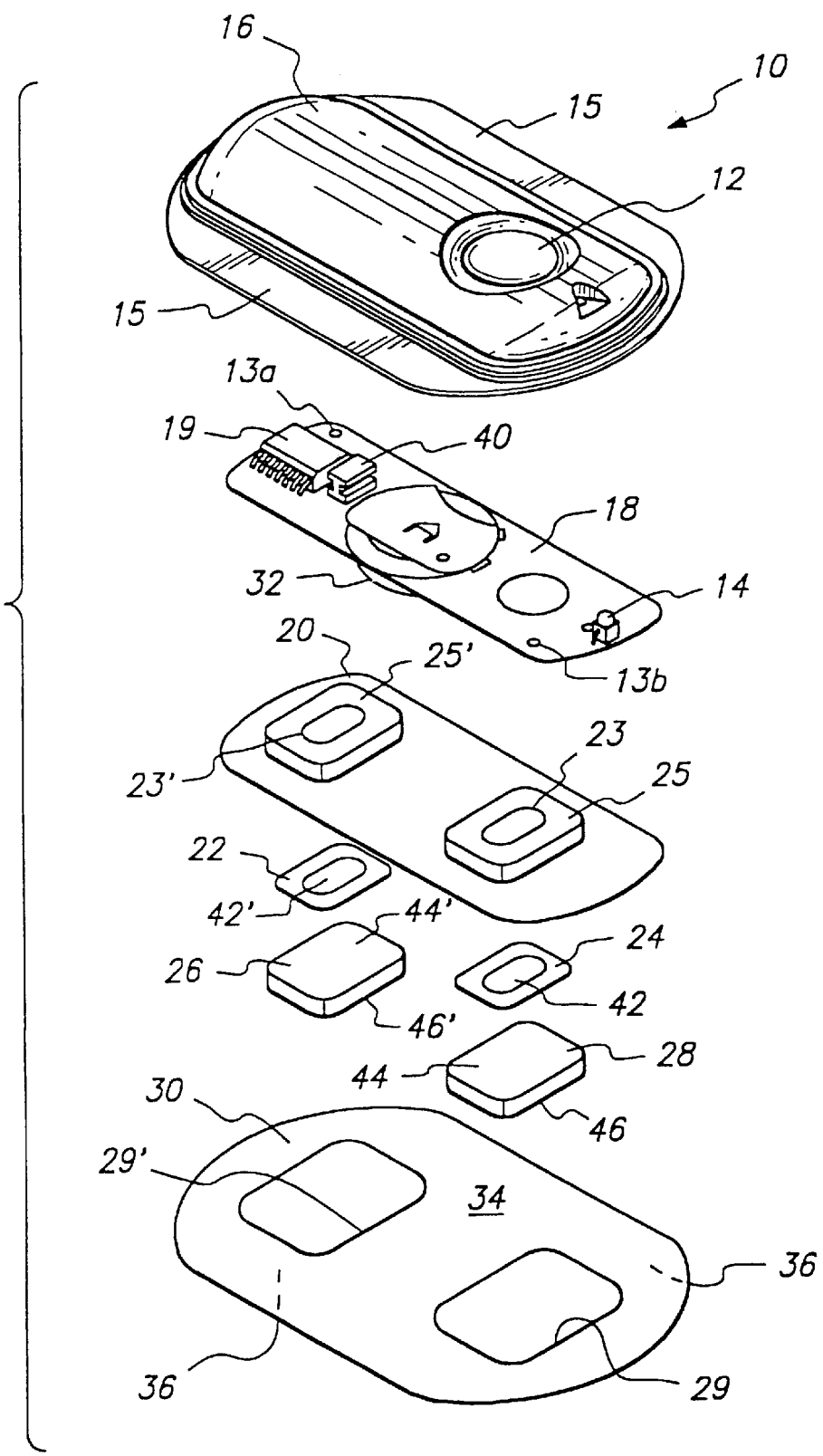
FIG. 1 is a perspective exploded view of one embodiment of an electrotransport drug delivery system which may be used in conjunction with drug formulations made using the inventive method.

Before describing the present invention in detail, it is to be understood that this invention is not limited to particular drugs, drug salts, resins or electrotransport delivery systems, as such may vary.

It must be noted that, as used in this specification and the appended claims, the singular forms "a", "an" and "the" include plural referents unless the content clearly dictates otherwise. Thus, for example, reference to "a drug" includes a mixture of two or more drugs, reference to "a resin" includes reference to one or more resins, and the like.

In describing and claiming the present invention, the following terminology will be used in accordance with the definitions set out below.

By the term "pharmaceutically active agent" or "drug" as used herein is meant any chemical material or compound which induces a desired local or systemic effect, and is capable of being delivered by electrotransport. Examples of such substances will be set forth below.

The terms "ion exchange resin" or "ion exchange material" are used herein to mean any material comprising (i) a mobile ionic species selected from the group consisting of hydronium and hydroxyl ions, and (ii) an oppositely charged, substantially immobile ionic species having the same charge as the drug to be delivered. The ion exchange materials useful in conjunction with the invention, as will be explained in detail below, are capable of donating either a hydroxyl ion (i.e., anion exchange resins, which are used to adjust the pH of cationic drug formulations), or a hydrogen ion (i.e., cation exchange resins, which are used to adjust the pH of anionic drug formulations).

By "neutralization" as used herein is meant conversion of ionized functionalities contained within the molecular structure of a drug to nonionic species, e.g., by converting carboxylate species to carboxylic acid moieties, by converting ammonium salts to amines, or the like. "Neutralization" for purposes of the present invention is generally "partial neutralization," in that only a fraction of the ionized functionalities present are converted to nonionic groups.

The method of the invention involves treatment of the drug to be administered prior to incorporation of the drug formulation into an electrotransport delivery system. This pre-treatment involves contacting a drug salt, wherein the drug may be either cationic or anionic, with a suitable ion exchange material.

With cationic drugs, the ion exchange material is an anion exchange material which will exchange hydroxyl ions for the negatively charged counterions typically used in conjunction with cationic drugs, e.g., chloride, bromide, acetate, trifluoroacetate, bitartrate, propionate, citrate, oxalate, succinate, sulfate, nitrate, phosphate, and the like. Suitable anion exchange materials are typically the hydroxide forms of amine-containing polymers, e.g., polyvinyl amines, poly epichlorohydrin/tetraethylenetriamines, polymers containing pendant amine groups, and the like. A preferred anion exchange material for use herein is a co-polymer of styrene and divinyl benzene having a quaternary ammonium functionality and an associated hydroxyl ion. Several such polymers are available within the "AG 1-X" family of resins from the Dow Chemical Company, e.g., AG 1-X2, AG 1-X4 and AG 1-X8. Other anion exchange materials include the hydroxide forms of Amberlite® IRA-958 (an acrylic/divinylbenzene copolymer available from Rohm and Haas), cholestyramine (a styrene/divinylbenzene copolymer also available from Rohm and Haas), Dowex 2X8 (a styrene/divinylbenzene available from Dow Chemical), and Macro-Prep High Q (an acrylic/ethyleneglycol dimethacrylate copolymer available from BioRad Laboratories). As will be appreciated by those skilled in the art, anion exchange materials containing primary, secondary and tertiary amines are relatively weak bases, while those containing quaternary amine functionalities are strongly basic, and will more quickly and effectively adjust upward the pH of formulations of cationic drug salts. Accordingly, such materials are preferred for use herein.

With anionic drugs, analogously, the ion exchange material used is a cation exchange material which will exchange hydrogen ions for the positively charged counterions typically used in conjunction with anionic drugs. Salts of cationic drugs are usually formed by treating the free acid form of the drug with a pharmaceutically acceptable base, typically an amine such as diethylamine, triethylamine, ethanolamine, or the like, giving rise to positively charged quaternary ammonium moieties associated with the drug. Cation exchange resins which will exchange hydrogen ions for such species include, for example, poly(acrylic acids), poly(acrylic sulfonic acids), poly(acrylic phosphoric acids) and poly(acrylic glycolic acids). Cation exchange resins containing carboxylic acid moieties are weaker acids, while those containing functionalities such as sulfonic acids will be more strongly acidic, and accordingly preferred in connection with the present method as providing faster and more efficient pH adjustment.

When preparing drug formulations adapted for electrotransport delivery through human skin, the preferred direction and type of pH adjustment will depend on whether the drug is cationic, and hence delivered from an anodic reservoir, or anionic and hence delivered from a cathodic reservoir, as well as on the solubility characteristics of the particular drug to be delivered. In general for electrotransport delivery through human skin, the pH of an anodic reservoir formulation is typically in the range of about 6 to 9, more preferably in the range of about 3.5 to 5. In general for electrotransport delivery through human skin, the pH of a cathodic reservoir is typically in the range of about 3 to 6, more preferably in the range of about 3.5 to 5.

It will be appreciated by those skilled in the art that conventional ion exchange materials, e.g., cation and anion exchange resins, may be replaced with any relatively high molecular weight material having acid or base functionalities, such that conversion of ionized functionalities present in the drug molecule will be effected by exchange with protons or hydroxyl ions present in the material, and separation of the drug formulation therefrom is facilitated by virtue of the material's molecular weight. Generally, although not necessarily, it is preferred that the molecular weight of the material be at least about 200 Daltons, more preferably at least about 300 Daltons, and most preferably at least about 500 Daltons.

The method of the invention is carried out by simple admixture of the ion exchange material, typically in the form of an ion exchange resin associated with a solid support (e.g., beads or the like), with a solution of the drug salt. The relative quantities of ion exchange material and drug salt will depend on the desired change in pH, which is in turn dependent on the degree of drug salt neutralization. Generally, the pH of the drug formulation will be adjusted such that the flux of the drug through the skin, during electrotransport drug delivery, is optimized. Accordingly, the preferred pH for any given drug salt formulation may be readily determined by conducting routine experimentation to evaluate optimum drug flux. For divalent or polyvalent drugs, neutralization is generally conducted to a degree effective to convert a substantial fraction of the drug salt, typically greater than about 80%, to a monovalent form; the inventors have found that monovalent drugs generally have a higher flux than their di- or polyvalent counterparts when delivered using electrotransport.

As noted above, drugs, therapeutic or active agents useful in connection with the present invention include any pharmaceutical compound or chemical that is capable of being delivered by electrotransport. In general, this includes agents in all of the major therapeutic areas including, but not limited to, anti-infectives such as antibiotics and antiviral agents, analgesics including fentanyl, sufentanil, buprenorphine and analgesic combinations, anesthetics, anorexics, antiarthritics, antiasthmatic agents such as terbutaline, anticonvulsants, antidepressants, antidiabetic agents, antidiarrheals, antihistamines, anti-inflammatory agents, antimigraine preparations, antimotion sickness preparations such as scopolamine and ondansetron, antinauseants, antineoplastics, antiparkinsonism drugs, antipruritics, antipsychotics, antipyretics, antispasmodics, including gastrointestinal and urinary anticholinergics, sympathomimetrics, xanthine derivatives, cardiovascular preparations including calcium channel blockers such as nifedipine, beta-blockers, beta-agonists such as dobutamine and ritodrine, antiarrythmics, antihypertensives such as atenolol, ACE inhibitors such as rinitidine, diuretics, vasodilators, including general, coronary, peripheral and cerebral, central nervous system stimulants, cough and cold preparations, decongestants, diagnostics, hormones such as parathyroid hormone, bisphosphoriates, hypnotics, immunosuppressives, muscle relaxants, parasympatholytics, parasympathomimetrics, prostaglandins, psychostimulants, sedatives and tranquilizers. The invention is also useful in conjunction with the electrotransport delivery of proteins, peptides and fragments thereof, whether naturally occurring, chemically synthesized or recombinantly produced.

Particular drugs of interest are alniditan ((−)-(R)-N-[(3,4-dihydro-2H-1-benzopyran-2-yl)methyl]-N'-(1,4,5,6-tetrahydropyrimidinyl)-1,3-propanediamine dihydrochloride) and its analogs, which are useful as antimigraine agents and have been found to be particularly suitable for electrotransport delivery. Further information concerning such agents may be found in PCT Publication No. WO93/17017 (DeBruyn et al.), the disclosure of which is incorporated by reference herein.

As noted hereinabove, the invention is also useful in the controlled delivery of peptides, polypeptides, proteins and other such species. These substances typically have a molecular weight of at least about 300 daltons, and more typically have a molecular weight of at least about 300 to 40,000 daltons. Specific examples of peptides and proteins in this size range include, without limitation, LHRH, LHRH analogs such as goserelin, buserelin, gonadorelin, napharelin and leuprolide, GHRH, GHRF, insulin, insultropin, calcitonin, octreotide, endorphin, TRH, NT-36 (chemical name: N-[[(s)-4-oxo-2-azetidinyl]carbonyl]-L-histidyl-L-prolinamide), liprecin, pituitary hormones (e.g., HGH, HMG, desmopressin acetate, etc), follicle luteoids, $\alpha$ANF, growth factors such as growth factor releasing factor (GFRF), $\beta$MSH, somatostatin, bradykinin, somatotropin, platelet-derived growth factor, asparaginase, chymopapain, cholecystokinin, chorionic gonadotropin, corticotropin (ACTH), erythropoietin, epoprostenol (platelet aggregation inhibitor), glucagon, HCG, hirulog, hyaluronidase, interferons, interleukins, menotropins (urofollitropin (FSH) and LH), oxytocin, streptokinase, tissue plasminogen activator, urokinase, vasopressin, desmopressin, ACTH analogs, ANP, ANP clearance inhibitors, angiotensin II antagonists, antidiuretic hormone agonists, bradykinin antagonists, CD4, ceredase, CSI's, enkephalins, FAB fragments, IgE peptide suppressors, IGF-1, neurotrophic factors, colony stimulating factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonists analogs, alpha-1 antitrypsin (recombinant), and TGF-beta.

Additional agents include fentanyl hydrochloride, pilocarpine nitrate, lidocaine hydrochloride, hydrocortisone derivatives, sodium salicylate, acetic acid, fluoride anion, lithium, antibiotics such as penicillin and cephalosporin and dexamethasone sodium phosphate, hydromorphone, diazepam salts, antihypertensive agents, bronchodilator agents, peptide hormone and regulatory agents and proteins.

Divalent and polyvalent drugs include, but are not limited to, alniditan, discussed above, as well as talipexole dihydrochloride, carpipramine dihydrochloride, histamine dihydrochloride, proflavine dihydrochloride and gusperimus trihydrochloride.

Reaction between the drug salt solution and the ion exchange material is typically quite fast, on the order of minutes. After the reaction is allowed to proceed to completion, the drug solution may be separated from the ion exchange material using standard filtration techniques (e.g., filters, screens, etc.) or using a syringe and a narrow gauge (e.g., 26 gauge) needle. The drug salt solution may then be introduced into the drug reservoir of an electrotransport delivery system, typically by incorporation into a gel matrix material which serves as the drug reservoir, as will be described below. In this manner, contamination with any extraneous species present in commercially available ion exchange materials are avoided, a problem inherent in those methods and systems in which ion exchange resins or the like are incorporated directly into the electrotransport delivery system. The method of the invention thus provides electrotransport drug delivery devices containing drug formulations which are substantially free of extraneous materials, particularly competitive ionic species. By "substantially free" is meant a formulation which contains less than about 0.1 wt. %, preferably less than about 0.01 wt. %, extraneous materials such as competitive ionic species or contaminants typically found in industrial grade resins.

It will be appreciated by those working in the field that the present method can be used in conjunction with a wide variety of electrotransport drug delivery systems, as the method is riot limited in any way in this regard. For examples of electrotransport drug delivery systems, reference may be had to U.S. Pat. Nos. 5,147,296 to Theeuwes et al., 5,080,646 to Theeuwes et al., 5,169,382 to Theeuwes et al., and 5,169,383 to Gyory et al, the disclosures of which are incorporated by reference herein.

FIG. 1 illustrates a representative electrotransport delivery device that may be used in conjunction with the present method. Device 10 comprises an upper housing 16, a circuit board assembly 18, a lower housing 20, anode electrode 22, cathode electrode 24, anode reservoir 26, cathode reservoir 28 and skin-compatible adhesive 30. Upper housing 16 has lateral wings 15 which assist in holding device 10 on a patient's skin. Upper housing 16 is preferably composed of an injection moldable elastomer (e.g., ethylene vinyl acetate). Printed circuit board assembly 18 comprises an integrated circuit 19 coupled to discrete components 40 and battery 32. Circuit board assembly 18 is attached to housing 16 by posts (not shown in FIG. 1) passing through openings 13a and 13b, the ends of the posts being heated/melted in order to heat stake the circuit board assembly 18 to the housing 16. Lower housing 20 is attached to the upper housing 16 by means of adhesive 30, the upper surface 34 of adhesive 30 being adhered to both lower housing 20 and upper housing 16 including the bottom surfaces of wings 15.

Shown (partially) on the underside of circuit board assembly 18 is a button cell battery 32. Other types of batteries may also be employed to power device 10.

The device 10 is generally comprised of battery 32, electronic circuitry 19,40, electrodes 22,24, and drug/chemical reservoirs 26,28, all of which are integrated into a self-contained unit. The outputs (not shown in FIG. 1) of the circuit board assembly 18 make electrical contact with the electrodes 24 and 22 through openings 23,23' in the depressions 25,25' formed in lower housing 20, by means of electrically conductive adhesive strips 42,42'. Electrodes 22 and 24, in turn, are in direct mechanical and electrical contact with the top sides 44',44 of drug reservoirs 26 and 28. The bottom sides 46',46 of drug reservoirs 26,28 contact the patient's skin through the openings 29',29 in adhesive 30.

Device 10 optionally has a feature which allows the patient to self-administer a dose of drug by electrotransport. Upon depression of push button switch 12, the electronic circuitry on circuit board assembly 18 delivers a predetermined DC current to the electrode/reservoirs 22,26 and 24,28 for a delivery interval of predetermined length. The push button switch 12 is conveniently located on the top side of device 10 and is easily actuated through clothing. A double press of the push button switch 12 within a short time period, e.g., three seconds, is preferably used to activate the device for delivery of drug, thereby minimizing the likelihood of inadvertent actuation of the device 10. Preferably, the device transmits to the user a visual and/or audible confirmation of the onset of the drug delivery interval by means of LED 14 becoming lit and/or an audible sound signal from, e.g., a "beeper". Drug is delivered through the patient's skin by electrotransport, e.g., on the arm, over the predetermined delivery interval.

Anodic electrode 22 is preferably comprised of silver and cathodic electrode 24 is preferably comprised of silver chloride. Both reservoirs 26 and 28 are preferably comprised of polymer hydrogel materials. Electrodes 22,24 and reservoirs 26,28 are retained by lower housing 20.

The push button switch 12, the electronic circuitry on circuit board assembly 18 and the battery 32 are adhesively "sealed" between upper housing 16 and lower housing 20. Upper housing 16 is preferably composed of rubber or other elastomeric material. Lower housing 20 is preferably composed of a plastic or elastomeric sheet material (e.g., polyethylene) which can be easily molded to form depressions 25,25' and cut to form openings 23,23'. The assembled device 10 is preferably water resistant (i.e., splash proof) and is most preferably waterproof. The system has a low profile that easily conforms to the body, thereby allowing freedom of movement at, and around, the wearing site. The reservoirs 26 and 28 are located on the skin-contacting side of the device 10 and are sufficiently separated to prevent accidental electrical shorting during normal handling and use.

The device 10 adheres to the patient's body surface (e.g., skin) by means of a peripheral adhesive 30 which has upper side 34 and body-contacting side 36. The adhesive side 36 has adhesive properties which assures that the device 10 remains in place on the body during normal user activity, and yet permits reasonable removal after the predetermined (e.g., 24-hour) wear period. Upper adhesive side 34 adheres to lower housing 20 and retains the electrodes and drug reservoirs within housing depression 25, 25' as well as retains lower housing 20 attached to upper housing 16.

The reservoirs 26 and 28 generally comprise a gel matrix, with the drug solution uniformly dispersed in at least one of the reservoirs 26 and 28. Drug concentrations in the range of approximately $1 \times 10^4$ M to 1.0 M or more can be used, with drug concentrations in the lower portion of the range being preferred. Suitable polymers for the gel matrix may comprise essentially any nonionic synthetic and/or naturally occurring polymeric materials. A polar nature is preferred when the active agent is polar and/or capable of ionization, so as to enhance agent solubility. Optionally, the gel matrix will be water swellable. Examples of suitable synthetic polymers include, but are not limited to, poly(acrylamide), poly(2-hydroxyethyl acrylate), poly(2-hydroxypropyl acrylate), poly(N-vinyl-2-pyrrolidone), poly(n-methylol acrylamide), poly(diacetone acrylamide), poly(2-hydroxylethyl methacrylate), poly(vinyl alcohol) and poly (allyl alcohol). Hydroxyl functional condensation polymers (i.e., polyesters, polycarbonates, polyurethanes) are also examples of suitable polar synthetic polymers. Polar naturally occurring polymers (or derivatives thereof) suitable for use as the gel matrix are exemplified by cellulose ethers, methyl cellulose ethers, cellulose and hydroxylated cellulose, methyl cellulose and hydroxylated methyl cellulose, gums such as guar, locust, karaya, xanthan, gelatin, and derivatives thereof. Ionic polymers can also be used for the matrix provided that the available counterions are either drug ions or other ions that are oppositely charged relative to the active agent.

Thus, after adjusting the pH of the drug solution using the method of the invention, the solution will be incorporated into the drug reservoir, e.g., a gel matrix as just described, and administered to a patient using an electrophoretic drug delivery system, optionally as exemplified hereinabove. Incorporation of the drug solution can be done any number of ways, i.e., by imbibing the solution into the reservoir matrix, by admixing the drug solution with the matrix material prior to hydrogel formation, or the like. By virtue of the way in which the pH of the formulation is adjusted prior to incorporation in an electrotransport delivery system, introduction of competitive ions or extraneous contaminants is avoided and drug flux is optimized Furthermore, since the formulation is a mixture of either (1) an acid and its salt or (2) a base and its salt, the formulation tends to have a stable pH, ie, the formulation is resistant to changes in pH resulting from addition of protons or hydroxyl ions.

While the invention has been described in conjunction with the preferred specific embodiments thereof, it is to be understood that the foregoing description as well as the examples which follow are intended to illustrate and not limit the scope of the invention. Other aspects, advantages and modifications within the scope of the invention will be apparent to those skilled in the art to which the invention pertains.

EXAMPLE 1

Partial neutralization of a drug salt using the method of the invention was carried out as follows.

The dihydrochloride salt of (−)-(R)-N-[(3,4-dihydro-2H-1-benzopyran-2-yl)methyl]-N'-(1,4,5,6-tetrahydropyrimidinyl)-1,3-propanediamine dihydrochloride

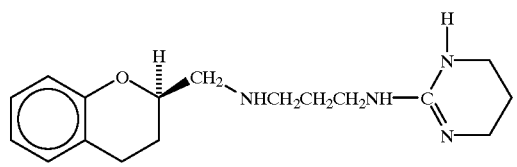

(1.25 g; obtained from Janssen Pharmaceutica) was added to 3.2 g water and stirred until completely dissolved. Additional water was added to provide 5.0 mL of solution. A 0.67 M solution of drug salt was thus provided, having a pH of approximately 4.24. Working from known pKa values for the secondary amine group (8.3) and the pyrimidinamine functionality (>11.0), the quantity of anion exchange resin (AG 1-X8, hydroxide form, obtained from Bio-Rad Laboratories) required to adjust the pH of the drug solution to 7.5 was calculated to be approximately 0.236 g (based on 1.71 meq OH$^-$ per 1.0 g resin). Accordingly, 0.236 g AG 1-X8 resin was added in portions to the drug solution until a pH of 7.49 was attained. The drug solution was removed from the resin by transferring with a pipet. Approximately 4.7–4.8 mL of drug solution was recovered. The solution may then be imbibed into a suitable hydrogel matrix or the like and incorporated into the drug reservoir of an electrotransport drug delivery device.

EXAMPLE 2

The procedure of Example 1 was repeated to neutralize a slightly more acidic solution of drug salt to a pH of 8.5. In order to do this, a 1.33 M solution of the dihydrochloride salt of (R-N-[(3,4-dihydro-2H-1-benzopyran-2-yl)methyl]-N'-(1,4,5,6-tetrahydro-2-pyrimidinyl)-1,3-propanediamine) was prepared by adding 2.50 g drug into water to give 5.0 mL total. The measured pH was 3.98. Again, based on known pKa values for the divalent salt, the quantity of anion exchange resin (AG 1-X8, hydroxide form, obtained from Bio-Rad Laboratories) required to adjust the pH of the drug solution to 8.5 was calculated to be approximately 2.47 g (based on 1.65 meq OH$^-$ per 1.0 g resin. The calculated quantity of AG 1-X8 resin was slowly added to the drug solution, with stirring, until a pH of 8.47 was attained (the pH was found to be fairly constant after neutralization was allowed to proceed for about 10 minutes). The drug solution was removed from the resin using a 3.0 mL plastic syringe and a 22 gauge needle. The solution may then be imbibed into a suitable hydrogel matrix or the like and incorporated into the drug reservoir of an electrotransport drug delivery device.

EXAMPLE 3

The procedure of Example 2 was repeated to partially neutralize a 1.33 M solution of drug salt (again, the dihydrochloride salt of (R-N-[(3,4-dihydro-2H-1-benzopyran-2-yl)methyl]-N'-(1,4,5,6-tetrahydro-2-pyrimidinyl)-1,3-propanediamine)) to a pH of 7.5. A 1.33 M solution was prepared as in Example 2, and 0.526 g resin was added. After neutralization was allowed to proceed for approximately 10 minutes, at which time the pH was found to be fairly constant, drug solution was removed using a 3.0 mL plastic syringe and a 22 gauge needle. The solution may then be imbibed into a suitable hydrogel matrix or the like and incorporated into the drug reservoir of an electrotransport drug delivery device.

EXAMPLE 4

Electrotransport Studies

Permeation Cell Assembly:

Electrotransport studies were conducted using two-compartment polycarbonate permeation cells designed to evenly support drug-containing hydrogels. A silver chloride extruded laminate was overlaid on an electrode support and sealed to the receptor compartment using double-sided adhesive tape. Human cadaver epidermis (abdomen, 2 cm$^2$) was adhered to the grid support on the receptor cell using adhesive tape, with the stratum corneum facing the donor compartment.

The drug-containing gels were seated into the anode housings consisting of a silver electrode and a foam mold. This assembled donor compartment was overlaid onto the epidermis and the electrode support secured to complete the permeation cell.

Heat-stripped human cadaver (abdomen) epidermis was used for the electrotransport studies. The epidermis was separated from the dermal layer by immersing the tissue in water at 60° C. for 90 seconds.

Donor reservoirs comprised of polyvinyl alcohol based hydrogels, each having an area of 2.0 cm$^2$ and a thickness of 0.16 cm, were prepared containing 15% polyvinyl alcohol and 2% hydroxypropylmethylcellulose. An aqueous 1.33 M solution of the drug salt of Example 1, ie, the dihydrochloride salt of (−)-(R)-N-[(3,4-dihydro-2H-1-benzopyran-2-yl)methyl]-N'-(1,4,5,6-tetrahydropyrimidinyl)-1,3-propanediamine was added to the gels as follows. Separate aliquots of the 1.33 M drug solution were adjusted to pH 5.0, pH 7.5, and pH 8.5 by the addition of an appropriate amount of the anion exchange resin (AG 1-X8, hydroxide form, obtained from Bio-Rad Laboratories). Separate hydrogels were imbibed with 32 µL of one of the three pH adjusted drug solutions to obtain hydrogels containing 12 mg of drug and respective pH's of 5.0, 7.5 and 8.5.

The receptor compartment of the permeation cell had a volume of 3.5 mL and was filled with full strength, 0.15 M Dulbecco's phosphate buffered saline ("DPBS"), pH 7.4.

The entire receptor solution sample was automatically collected every fifteen minutes for the four hour transdermal flux study.

Analytical Methods:

The receptor solution samples were analyzed by injecting 20 μL samples onto a Alltech Hypersil BDS C18 column (100 mm×4.6 mm). The column temperature was ambient and the mobile phase was 97% 0.01 M tetrabutylammonium hydrogen sulfate and 3% acetonitrile (the flow rate was 1 mL/min).

The following table contains a summary of the data obtained over the 0.5 to 4 hour testing period:

| Cells | pH | Current Density (mA/cm$^2$) | Avg. Transdermal Flux (μg/cm$^2$h) |
|---|---|---|---|
| 1 | 5.0 | 0.200 | 220 ± 20 |
| 2 | 7.5 | 0.200 | 300 ± 20 |
| 3 | 8.5 | 0.200 | 440 ± 50 |

Figure 2:
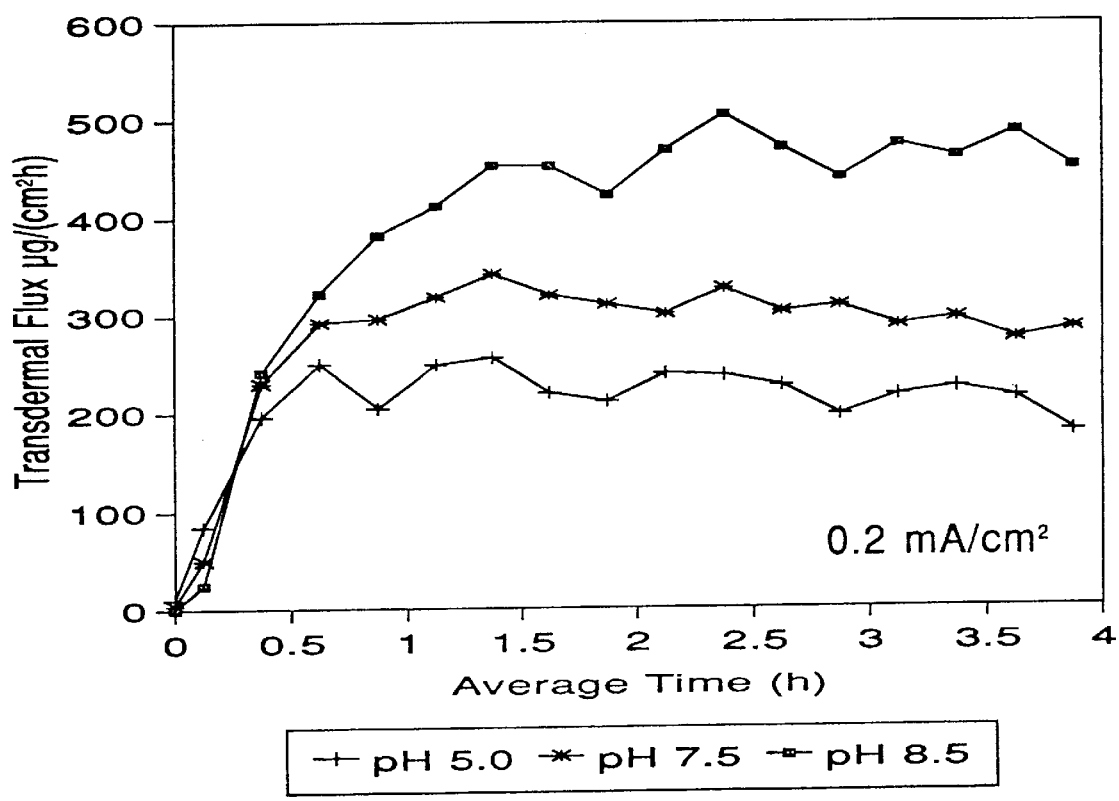
FIG. 2 is a graph illustrating the effect of pH adjustment on drug flux over a four-hour evaluation period, as described in Example 4.

A graph of flux versus time is shown in FIG. 2. As may be seen therein, increasing the pH of the drug formulation significantly increases the flux of the drug through skin, over virtually the entire four-hour period evaluated.

I claim:

1. A process for making a pH adjusted composition in an electrotransport delivery system comprising:
   providing a drug solution including drug ions and drug counter ions, the solution having a pH;
   adjusting the pH of the drug solution by contacting the solution with an ion exchange material and exchanging hydronium or hydroxyl ions for the counter ions;
   separating the ion exchange material from the pH-adjusted solution; and
   adding the pH-adjusted solution to a reservoir of an electrotransport delivery system.

2. The process of claim 1, wherein said removing of the material is accomplished by filtering the solution.

3. The process of claim 1, wherein the solution is an aqueous solution.

4. The process of claim 1, wherein the drug comprises a cationic drug having a negatively charged counterion associated therewith, and the material is an anion exchange resin.

5. The process of claim 4, wherein the step of adjusting the pH further includes adjusting the pH of the solution to within about pH 6 to 9.

6. The process of claim 4, wherein the step of adjusting the pH further includes adjusting the pH of the solution to within about pH 7.5 to 8.5.

7. The process of claim 4, wherein the anion exchange resin comprises a hydroxide form of an amine-containing polymer.

8. The process of claim 7, wherein the amine-containing polymer is selected from the group consisting of polyvinyl amines, polyepichlorohydrin/tetraethylenetriamines, copolymers of styrene and divinyl benzene, acrylic/divinyl benzene copolymers, and acrylic/ethyleneglycol dimethacrylate copolymers.

9. The process of claim 1, wherein the drug comprises a multivalent cationic drug having negatively charged counterions associated therewith.

10. The process of claim 1, wherein the drug comprises an anionic drug having a positively charged counterion associated therewith, and the material is a cation exchange resin.

11. The process of claim 10, wherein the step of adjusting the pH further includes adjusting the pH of the solution to within about pH 3 to 6.

12. The process of claim 10, wherein the step of adjusting the pH further includes adjusting the pH of the solution to within about pH 3.5 to 5.

13. The process of claim 10, wherein the cation exchange resin comprises a polymer having one or more acid moieties.

14. The process of claim 13, wherein the polymer is selected from the group consisting of poly(acrylic acids), poly(acrylic sulfonic acids), polyacrylic phosphoric acids) and poly(acrylic glycolic acids).

15. The process of claim 1, wherein the pH adjusting is accomplished by reacting the drug with the material for a time sufficient to allow the desired degree of pH adjustment to occur.

16. The process of claim 1, wherein the pH-adjusted drug formulation is added to a donor reservoir of an electrotransport delivery system.

17. The process of claim 16, wherein the donor reservoir comprises a gel.

18. The process of claim 1, wherein the pH of the solution is adjusted to a level which exhibits a higher electrotransport drug flux through the body surface compared to drug flux at another pH level.

19. A donor reservoir formulation made according to the process of claim 1.

* * * * *